US00PP24467P3

(12) United States Plant Patent
Head et al.

(10) Patent No.: US PP24,467 P3
(45) Date of Patent: May 20, 2014

(54) AZALEA PLANT NAMED 'RLH1-12P0'

(50) Latin Name: *Rhododendron hybrida*
Varietal Denomination: RLH1-12P0

(71) Applicants: Robert Harold Head, Seneca, SC (US); Lisa Jones Head, Seneca, SC (US)

(72) Inventors: Robert Harold Head, Seneca, SC (US); Lisa Jones Head, Seneca, SC (US)

(73) Assignee: Head's Select, Inc., Seneca, SC (US)

( * ) Notice: Subject to any disclaimer, the term of this patent is extended or adjusted under 35 U.S.C. 154(b) by 0 days.

(21) Appl. No.: 13/573,832

(22) Filed: Oct. 8, 2012

(65) Prior Publication Data

US 2014/0101803 P1 Apr. 10, 2014

(51) Int. Cl.
*A01H 5/00* (2006.01)

(52) U.S. Cl.
USPC ..... Plt./239

(58) Field of Classification Search
USPC ..... Plt./239, 238, 240
See application file for complete search history.

*Primary Examiner* — Kent L Bell
(74) *Attorney, Agent, or Firm* — C. A. Whealy

(57) ABSTRACT

A new and distinct cultivar of Azalea plant named 'RLH1-12P0', characterized by its compact, upright to outwardly spreading and mounding plant habit; freely basal branching habit; dense and bushy appearance; vigorous growth habit and rapid growth rate; evergreen, persistent dark green-colored leaves that do not abscise during the winter; freely flowering habit with remontant flowering during the spring, summer and autumn; large, non-persistent single flowers that are light pink in color with red purple-colored central spots and speckles; and excellent garden performance and temperature tolerance.

1 Drawing Sheet

Botanical designation: *Rhododendron hybrida.*
Cultivar denomination: 'RLH1-12P0'.

BACKGROUND OF THE INVENTION

The present Invention relates to a new and distinct cultivar of Azalea plant, botanically known as *Rhododendron hybrida*, commercially referred to as an evergreen Azalea plant and hereinafter referred to by the name 'RLH1-12P0'.

The new Azalea plant is a product of a planned breeding program conducted by the Inventors in Long Creek, Oconee County, S.C. The objective of the breeding program is to create new compact evergreen Azalea plants having dense growth habit, large attractive flowers, flowers with good temperature tolerance, consistent remontant flowering during the spring, summer and autumn, good garden performance and low and high temperature tolerance.

The new Azalea plant originated from a cross-pollination made by the Inventors in 1996 in Long Creek, Oconee County, S.C., of a proprietary selection of *Rhododendron hybrida* identified as code number RLH-1800-WS, not patented, as the female, or seed, parent with *Rhododendron hybrida* 'Watchet', not patented, as the male, or pollen, parent. The new Azalea plant was discovered and selected by the Inventors as a single flowering plant within the progeny of the stated cross-pollination in a controlled greenhouse environment in Long Creek, Oconee County, S.C. in 2000.

Asexual reproduction of the new Azalea plant by semi-hardwood stem cuttings taken in a controlled greenhouse environment in Long Creek, Oconee County, S.C. since 2005 has shown that the unique features of this new Azalea plant are stable and reproduced true to type in successive generations.

SUMMARY OF THE INVENTION

Plants of the new Azalea have not been observed under all possible environmental conditions and cultural practices. The phenotype may vary somewhat with variations in environmental conditions such as temperature, daylength and light intensity without, however, any variance in genotype. The following traits have been repeatedly observed and are determined to be the unique characteristics of 'RLH1-12P0'. These characteristics in combination distinguish 'RLH1-12P0' as a new and distinct Azalea plant:

1. Compact, upright to outwardly spreading and mounding plant habit.
2. Freely basal branching habit; dense and bushy appearance; vigorous growth habit and rapid growth rate.
3. Evergreen, persistent dark green-colored leaves that do not abscise during the winter.
4. Freely flowering habit with remontant flowering during the spring, summer and autumn.
5. Large, non-persistent single flowers that are bright pink in color with red purple-colored central spots and speckles.
6. Excellent garden performance and temperature tolerance.

Plants of the new Azalea differ primarily from plants of the female parent selection in the following characteristics:

1. Plants of the new Azalea are more spreading than and not as upright as plants of the female parent selection.
2. Plants of the new Azalea have larger flowers than plants of the female parent selection.
3. Plants of the new Azalea and the female parent selection differ in flower color as plants of the female parent selection have darker pink-colored flowers.

Plants of the new Azalea differ primarily from plants of the male parent, 'Watchet', in the following characteristics:

1. Plants of the new Azalea are more mounding than and not as globose as plants of 'Watchet'.
2. Plants of the new Azalea have smaller leaves than plants of 'Watchet'.

3. Plants of the new Azalea and 'Watchet' differ slightly in flower color.

Plants of the new Azalea can be compared to the plants of 'Robleg', disclosed in U.S. Plant Pat. No. 15,227. In side-by-side comparisons conducted in Long Creek, Oconee County, S.C., plants of the new Azalea differed primarily from plants of 'Robleg' in the following characteristics:

1. Plants of the new Azalea were more uniform in plant shape and required less pruning to maintain a more uniform shape than plants of 'Robleg'.
2. Plants of the new Azalea were more freely flowering than plants of 'Robleg'.
3. Flower petals of plants of the new Azalea were more undulate than flower petals of plants of 'Robleg'.
4. Plants of the new Azalea and 'Robleg' differed in flower color as plants of 'Robleg' had white-colored flowers.
5. Plants of the new Azalea flowered during the spring, summer and autumn whereas plants of 'Robleg' only flowered during the spring and autumn.
6. Plants of the new Azalea were more cold hardy than plants of 'Robleg'.

BRIEF DESCRIPTION OF THE PHOTOGRAPH

The accompanying colored photograph illustrates the overall appearance of the new Azalea plant showing the colors as true as it is reasonably possible to obtain in colored reproductions of this type. Colors in the photograph may differ slightly from the color values cited in the detailed botanical description which accurately describe the colors of the new Azalea plant. Plants used for the photograph were grown during the late summer in ground beds in a shady outdoor nursery in Long Creek, Oconee County, S.C. and under cultural practices which approximate commercial Azalea production. During the production of the plants, day temperatures ranged from 0° C. to 45° C. and night temperatures ranged from −17° C. to 38° C. Plants were seven years old when the photograph were taken.

The photograph comprises a top perspective view of typical flowering plants of 'RLH1-12P0'.

DETAILED BOTANICAL DESCRIPTION

The following observations and measurements describe plants grown during the late summer in three-gallon containers in a shadehouse in El Campo, Tex. and under cultural practices which approximate commercial Azalea production. During the production of the plants, day temperatures averaged 24° C. and night temperatures averaged 14° C. Plants were one year old when the detailed description was taken. In the following description, color references are made to The Royal Horticultural Society Colour Chart, 2007 Edition, except where general terms of ordinary dictionary significance are used.

Botanical classification: *Rhododendron hybrida* 'RLH1-12P0'.

Commercial classification: Evergreen Azalea.

Parentage:

*Female, or seed, parent*.—Proprietary selection of *Rhododendron hybrida* identified as code number RLH-1800-WS, not patented.

*Male, or pollen, parent*.—*Rhododendron hybrida* 'Watchet', not patented.

Propagation:

*Type*.—By semi-hardwood stem cuttings.

*Time to initiate roots, summer*.—About 25 to 30 days at temperatures of 27° C. to 30° C.

*Time to initiate roots, winter*.—About 35 to 45 days at temperatures of 16° C. to 17° C.

*Time to produce a rooted young plant, summer*.—About 60 to 70 days at temperatures of 27° C. to 30° C.

*Time to produce a rooted young plant, winter*.—About 80 to 100 days at temperatures of 16° C. to 17° C.

*Root description*.—Fine, fibrous; initially white in color becoming light brown with development.

*Rooting habit*.—Freely branching; dense.

Plant description:

*Plant form, plant and growth habit*.—Perennial and evergreen flowering subshrub; compact, upright to outwardly spreading and mounding plant habit; vigorous growth habit; rapid growth rate; freely flowering habit with numerous single flowers.

*Branching habit*.—Freely branching habit with lateral branches potentially developing at every node; dense and bushy appearance; pinching (removal of terminal apex) enhances lateral branch development.

*Plant height, soil level to top of flowers*.—About 20 cm.

*Plant diameter, area of spread*.—About 43 cm.

*Lateral branch description*.—Length: About 9 cm to 21 cm. Diameter at base: About 4.5 mm. Internode length: About 1 cm. Strength: Strong. Aspect: Upright to outwardly spreading. Texture, developing: Pubescent, fine rusty brown-colored hairs. Texture, mature: Woody; pubescent, fine rusty brown-colored hairs. Color, developing: Close to 146C. Color, semi-hardwood: Close to 146B to 146C becoming close to 165A with development. Color, mature: Close to 165A.

*Leaf description*.—Arrangement: Alternate; simple. Leaf retention: Very good winter leaf retention has been observed on plants of the new Azalea. Length: About 4.25 cm. Width: About 2.2 cm. Shape: Obovate to oblanceolate or elliptic. Apex: Mucronate. Base: Cuneate to attenuate. Margin: Entire; slightly revolute; ciliate. Venation pattern: Pinnate; reticulate. Texture, upper and lower surfaces: Pubescent; coriaceous, tough. Color: Developing leaves, upper surface: Between 137A and N137C. Developing leaves, lower surface: Close to 137B to 137C. Fully expanded leaves, upper surface: Close to N137A to N137C; venation, close to 146B. Fully expanded leaves, lower surface: Close to 146B; venation, close to 146C. Petioles: Length: About 7.5 mm. Diameter: About 2 mm. Texture, upper and lower surfaces: Pubescent. Color, upper surface: Close to 146B. Color, lower surface: Close to 146C.

Flower description:

*Natural flowering season*.—Spring, April to May, and then remontant flowering during the summer and autumn, July to October or until frost in USDA Hardiness Zone 6.

*Flower appearance and arrangement*.—Single flowers arranged upwardly to outwardly in clusters at terminals and sub-terminals; single whorl of five petals fused towards the base.

*Flowering habit*.—Freely flowering habit with usually about one to three to five flowers per cluster.

*Flower longevity*.—Flowers are durable and long-lasting; depending on the temperature, flowers last about one week on the plant; flowers not persistent.

*Fragrance*.—None detected.

*Flower diameter*.—About 8.25 cm.

*Flower depth*.—About 4.5 cm.

*Flower buds* (*before showing color*).—Length: About 1 cm. Diameter: About 5 mm. Shape: Ovoid. Color: Close to 144A.

*Petals*.—Length: About 5 cm. Width: About 3.5 cm. Shape: Broadly ovate to orbicular; roughly spatulate. Apex: Rotund; undulate; occasionally retuse. Margin: Entire; undulate. Texture, upper and lower surfaces: Smooth, glabrous; rugulose; waxy to velvety in appearance. Color: When opening, upper surface: Close to 50B to 50C; central spots and speckles, close to N66B. When opening, lower surface: Close to 50B to 50C. Fully opened, upper surface: Close to 50C and 52C to 52D; spots and speckles, close to N66A to N66B. Fully opened, lower surface: Close to 50C and 52D.

*Sepals*.—Arrangement: Five in a single whorl, fused at the base forming a campanulate to star-shaped corona. Length: About 7.5 mm. Width: About 3.5 mm. Shape: Lanceolate. Apex: Acute. Base: Fused. Margin: Entire; ciliate. Texture, upper and lower surfaces: Densely pubescent. Color, upper and lower surfaces: Close to 144A.

*Peduncles*.—Length: About 1.3 cm. Diameter: About 2 mm. Angle: Mostly upright to outwardly. Strength: Strong; flexible. Texture: Pubescent. Color: Close to 144B to 144C.

*Reproductive organs*.—Androecium: Quantity of stamens per flower: About five. Filament length: About 2.6 cm to 3.2 cm. Filament color: Close to NN155D. Anther shape: Porandrous with four oblong, tubular to lunate-shaped pollen sacks basifixed to the filament. Anther length: About 2.5 mm. Anther color: Close to 172A. Pollen amount: None. Gynoecium: Pistil length: About 3.3 cm. Stigma shape: Round to flattened (capitate). Stigma color: Close to 163A. Style length: About 2.75 cm. Style color: Close to 160A. Ovary color: Close to 139A.

*Fruits and seeds*.—Fruit and seed development have not been observed on plants of the new Azalea.

Garden performance & temperature tolerance: Plants of the new Azalea have been observed to be very tolerant to rain, wind and temperatures ranging from about −25° C. to about 45° C.; and plants of the new Azalea are suitable for USDA Hardiness Zones 6 to 9.

Disease & pest resistance: Plants have not been observed to be resistant to pathogens and pests common to Azalea plants.

It is claimed:

1. A new and distinct cultivar of Azalea plant named 'RLH1-12P0' as illustrated and described.

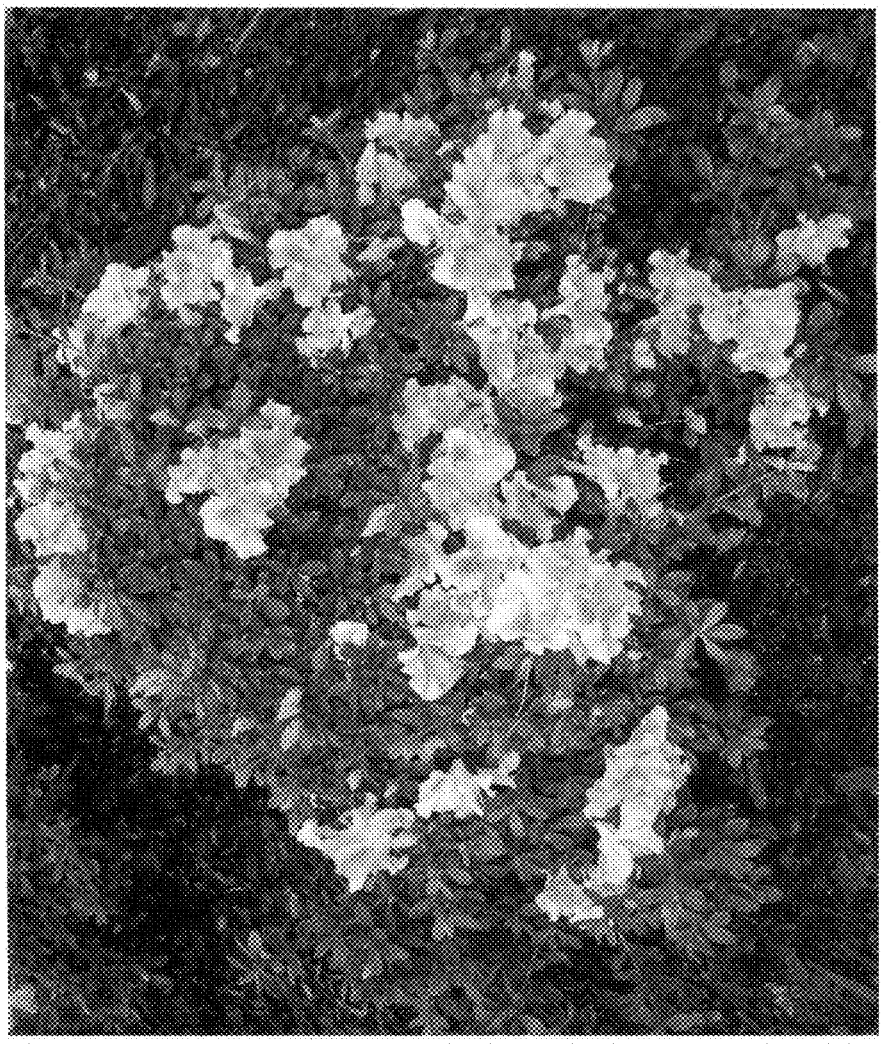

* * * * *